United States Patent [19]
Weijand et al.

[11] Patent Number: 5,836,983
[45] Date of Patent: Nov. 17, 1998

[54] OUTPUT STAGE WITH SWITCHABLE CONSTANT CURRENT MODES

[75] Inventors: Koen J. Weijand, Hoensbroek; Robert Leinders, Limbricht, both of Netherlands

[73] Assignee: Medtronic, Inc., Minneapolis, Minn.

[21] Appl. No.: 879,214

[22] Filed: Jun. 19, 1997

Related U.S. Application Data

[63] Continuation of Ser. No. 585,216, Jan. 11, 1996, abandoned.
[51] Int. Cl.$^6$ .................................................. A61N 1/362
[52] U.S. Cl. ................................ 607/9; 607/68; 607/72; 607/32; 607/60
[58] Field of Search .................................. 607/9, 11, 27, 607/29, 30, 32, 68, 59, 60, 72

[56] References Cited

U.S. PATENT DOCUMENTS

| | | | |
|---|---|---|---|
| 4,340,062 | 7/1982 | Thompson et al. | 128/419 PG |
| 4,416,282 | 11/1983 | Saulson et al. | 128/419 PG |

OTHER PUBLICATIONS

Breivik, K. et al., "Electrophysiological Properties of a New Permanent Endocardial Lead for Uni–and Bipolar Pacing," PACE 5, Mar.–Apr. 1982, pp. 268–274.

Ector et al., "Measurement of Pacing Threshold," PACE 8, Jan.–Feb. 1985, pp. 66–72.

Hogan, James F. et al., "Electrical Techniques for Stimulation of the Phrenic Nerve to Pace the Diaphragm: Inductive Coupling and Battery Powered Total Implant in Asynchronous and Demand Modes," PACE, vol. 12, May 1989, pp. 847–853.

"Pulse Generator Output Stage With Programmable Output Voltage," Research Disclosure, Jun. 1993, p. 374.

*Primary Examiner*—Jeffrey R. Jastrzab
*Attorney, Agent, or Firm*—Michael J. Jaro; Harold Patton

[57] ABSTRACT

An output circuit is provided for delivering output pulses in either a constant voltage or constant current mode. The output circuit has a simple architecture built around a pair of area-ratioed transistors which operate in a linear range carrying a ratio of currents corresponding to the area ratio. The circuit is mode controlled by a switch network which connects to a constant current source, which constant current source controls the pulse amplitude, either current or voltage. As used in a pacemaker embodiment, the circuit is controllable to control the mode and/or amplitude of the pulse following a cyclical decision to deliver a pulse, and with an amplitude derived from pacemaker data and controllable during delivery of the pulse. The circuit has high speed control which enables amplitude modulation of the pulse, for transmitting encoded data to an external device adapted to receive the data.

27 Claims, 4 Drawing Sheets

5,836,983

1
OUTPUT STAGE WITH SWITCHABLE CONSTANT CURRENT MODES

This is a continuation of application Ser. No. 08/585,216 filed on Jan. 11, 1996 now abandoned.

BACKGROUND OF THE INVENTION

This invention relates to controllable output stages for delivering either constant voltage or constant current outputs and, in particular, an output stage suitable for use in delivering a stimulus output in a cardiac pacemaker or similar medical device and which can be programmed to deliver the output in a selected constant current or constant voltage mode, and also amplitude modulated to carry encoded data.

In any medical device, such as a pacemaker or nerve stimulator, which must be capable of generating and delivering cyclical stimulus pulses, there is a need for an efficient and controllable output stage for shaping and delivering the pulses with the requisite power and shape. Particularly with programmable implanted devices, such as most pacemakers, it is not sufficient to have an output stage which simply reacts to a trigger. What is desirable is the capability to control the output pulse, when the time trigger occurs, and in accordance with programmed instructions, so that a variety of different pulse shapes can be delivered efficiently, and exactly as programmed.

In the pacemaker prior art, the substantially universal method of generating an output stimulus is designed around the central feature of charging a capacitor, and then discharging the capacitor at the proper time and with predetermined discharge characteristics. There are a great many examples in the pacemaker art of various output circuits for controlling capacitor discharge and recharge, so as to deliver stimulus pulses of different shapes, eg, biphaisc and triphasic pulses. However, these circuits involve considerable complexity, and indeed the more control over the pulse, the more complicated the switching circuitry must be. The ability to control the timing and waveform of the pulse is limited by the need to re-adjust the capacitor charge. Further, in pacing and other applications, it is frequently desirable to have the capability of providing for either constant voltage or constant current outputs, which likewise can be achieved, but at the cost of more complicated control circuitry. For examples of circuits adapted to provide constant voltage, constant current, or both modes, see U.S. Pat. Nos. 4,340,062 and 4,416,282, and "Measurement of Pacing Threshold", Ector et al, PACE 8, pp 66–72, January–February 1985.

However, there remains a need in the art for an output circuit design which is more efficiently controllable, both in terms of output mode and in terms of high speed switching and pulse shape. Particularly for implantable devices or battery-supplied devices, it is important that the output stage be efficient in converting battery power into the desired output shape, and that it be switchable at high speed so as to provide precisely the programmed waveform.

SUMMARY OF THE INVENTION

It is a primary object of this invention to achieve an improvement over the prior art whereby there is provided an output stage, or circuit, which uses a minimal number of components and is programmable to provide outputs in either a constant current or constant voltage mode, has maximum capability for accurate and high frequency pulse shape control, and is extremely power efficient. It is a further object to provide an output stage for an implanted device such as a pacemaker, and which is controllable so as to encode data on the output stimulus which can be received and decoded externally by simple surface electrodes on the patient, making data transmission from the patient possible without sophisticated telemetry equipment.

The circuit of this invention meets the above requirements with a minimum of components which can easily be fabricated on a chip. Further, the high speed control which is provided makes possible amplitude modulation of the output pulse for use in data transmission to a simple external pick-up such as surface electrodes. The circuit of this invention provides for control of the pulse characteristics during delivery of the pulse, and is particularly useful for applications calling for delivery of a multiphasic stimulus having different amplitudes, e.g., pacemakers or neurological stimulators.

In accordance with the above objects, there is provided a high speed switchable output stage which is constructed of just one op-amp and two transistors, the transistors preferably having an area ratio that controls the respective currents through the two transistors to be of the same ratio. The stage uses a novel architecture which provides the output at the same node for either mode of operation. A programmable low value current source is switched alternately into one or the other of the op-amp inputs with the other input grounded, depending on whether the output is to operate in constant voltage or constant current mode. The output of the op-amp is connected to the inputs of the two transistors, suitably "Gridmos" or GMOS transistors, each having its output connected to the stage output, and which are operated in their linear range so that they carry respective currents of a fixed proportion, e.g., the first carries about 200 times as much as the second. In the constant voltage mode, the constant current source is connected to the negative op-amp input and also connected directly through a resistor to the output, holding the output at a constant voltage from the virtual ground of the op-amp. In the constant current mode, the current source is connected to the positive op-amp input, and also to the lower current transistor, thereby controlling the current output of both transistors and thus the load current. In either mode, the circuit acts as a linear variable element in series with the device voltage source and the output load. The circuit is very simple but very efficient, and draws no current when inactive. In a medical device embodiment, the output circuit can be used to deliver multichannel, or multiphasic pulses of different amplitude; this can be done because no time is required for recharging a capacitor.

The invention also provides, in a unique application of the output stage, a system and method of amplitude modulation encoding of bits onto the output pulses. Since the output can be changed within a 2–10 microsecond interval, a 16 bit word can be encoded onto a 200 microsecond pulse.

3C is an equivalent circuit diagram of the output stage when in the constant current mode.

Figure 4A:
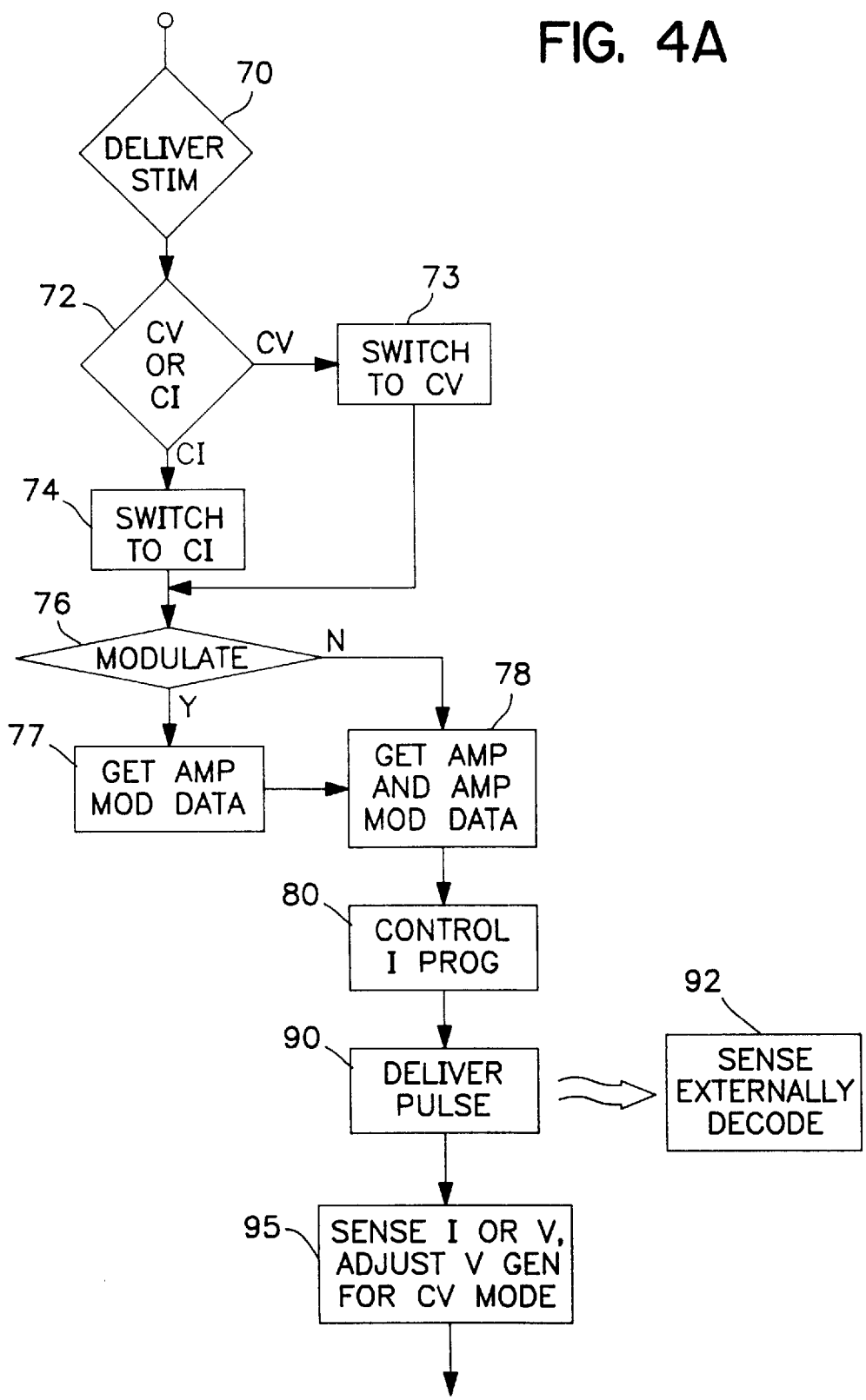
Figure 4B:
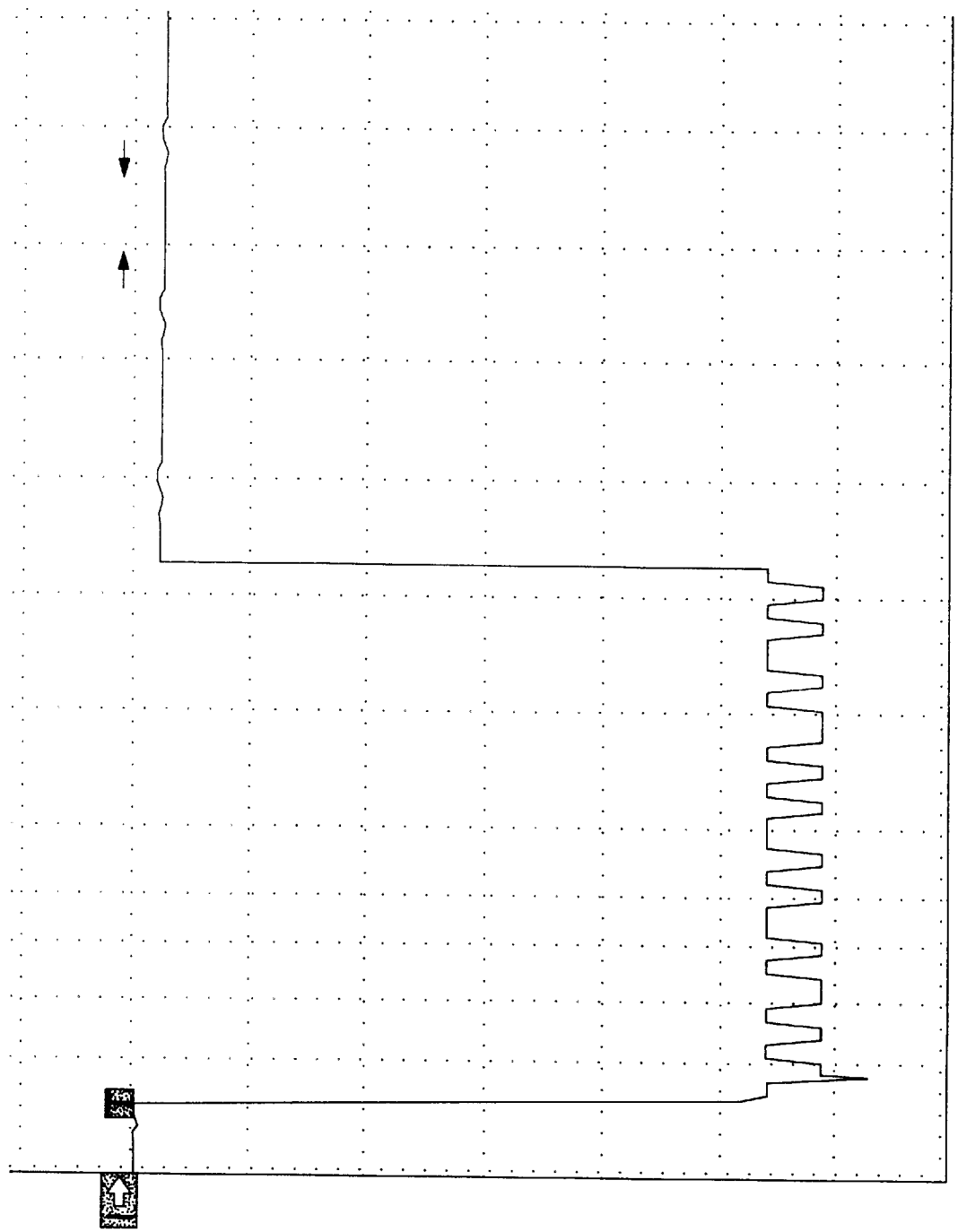

FIG. 4A is a flow diagram of the primary steps taken in controlling the pulse generator in accordance with this invention, as well as encoding data onto a delivered pulse and in sensing and decoding the data; FIG. 4B is an illustration of a waveform modulated in accordance with this invention to carry encoded data.

DESCRIPTION OF THE PREFERRED EMBODIMENTS

Referring to the drawings, there are illustrated preferred embodiments of the invention, illustrated with specific components and combinations of elements. It is to be understood that while the preferred embodiment is in the pacemaker art, certain aspects of the invention are very applicable to other art areas, and equivalent components can be used within the scope of the invention.

Figure 1:
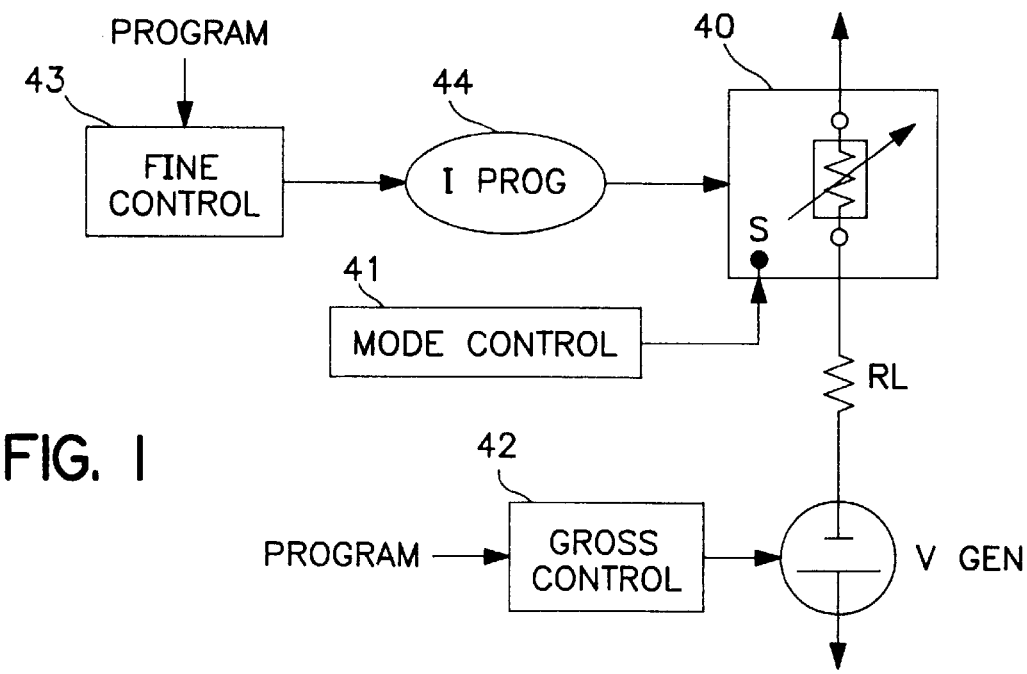
FIG. 1 is a diagram illustrating the simple architecture of the output circuit, and the manner of control.

Looking specifically at FIG. 1, there is shown a schematic which illustrates how use of a linear regulating element, or circuit 40, is the central element of the regulator architecture used in this invention. A regulating element, or elements, are placed in series with the load designated as R1 and the voltage generator, which is suitably a battery. Circuit 40 is coupled to a programming current, $I_{prog}$ as shown at 44, which in turn is established by programmable fine control 43. Additionally, circuit 40 is placed in a constant voltage or constant current mode by operation of mode control 41, which controls a switch network as indicated at S. A voltage generator, or battery, designated as $V_{GEN}$, is controlled by programmable gross control 42. For example, this control may be accomplished by connecting capacitors to the battery when there is no pulse being generated, and by connecting the capacitors in series or parallel when a pulse is required, in a known fashion. This provides a gross programming of output level for the constant voltage mode. The programming current can be controlled in predetermined increments, by known methods of controlling current sources, for "fine" tuning, or control of either the constant voltage or constant current outputs.

Figure 2:
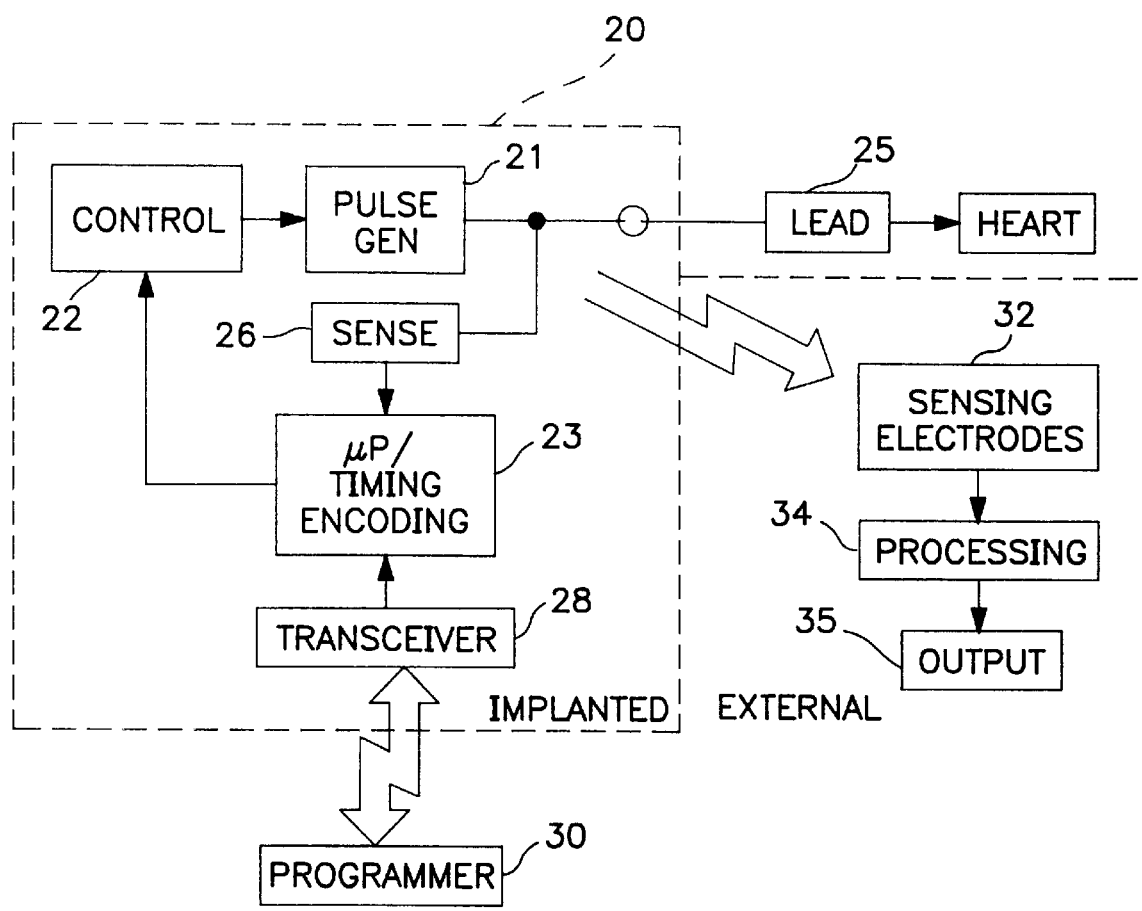
FIG. 2 is a block diagram of a system incorporating the primary components of an implantable device with the output stage of this invention, and also illustrating external components for programming the implanted device, and for externally picking up data encoded onto stimulus pulses delivered by the output stage.

Referring now to FIG. 2, there is shown a simple block diagram of an implantable pacemaker, which is illustrative of the class of medical devices within the scope of this invention as claimed. Pulse generator 21 is the output stage, which actually generates stimulus pulses. It is controlled, in terms of timing and amplitude, by control circuit 22. Circuit 22, in turn, receives timing and amplitude data from microprocessor block 23. As is prevalent in implantable pacemakers, this block may incorporate not just a microprocessor, but also associated memory, analog circuits for timing and the like, and in this embodiment, also encoding circuitry for encoding data on the control signals coupled to control 22. Further, the pacemaker may be in communication with an external programmer of known type, as shown at 30, for receiving program control data.

Further as shown in FIG. 2, the system of this invention may include sensing electrodes 32, preferably surface electrodes, for sensing the waveform of delivered stimulus pulses, which are delivered through lead 25 to the patient's heart. As explained in greater detail below, the pulses are amplitude-modulated, and by the use of simple surface electrodes this modulation can be decoded to provide data which had been collected and stored in pacemaker 22. The sensed signals are processed at block 34, and outputted at block 35.

Figure 3A:
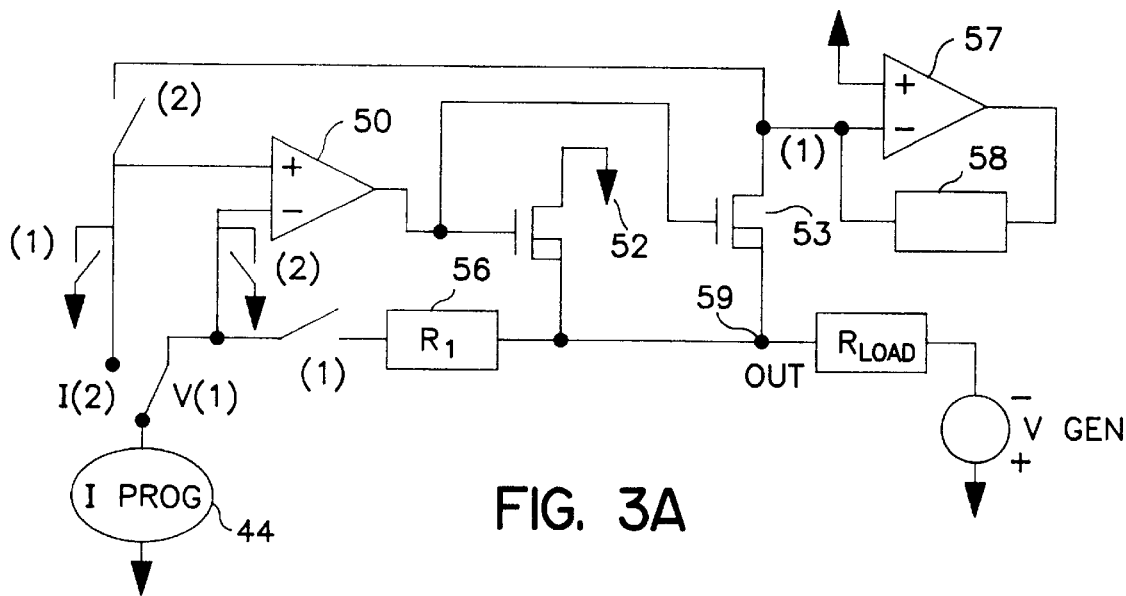
FIG. 3A is a circuit diagram of the output stage of this invention.

Referring to FIG. 3A, the circuit diagram of the output stage is now explained. The switches are each marked as either (1), corresponding to the constant voltage mode, or (2), corresponding to the constant current mode. The switches are set to one of the two modes by control circuit 22, which acts upon information sent from block 23. In the constant voltage mode, the current source $I_{prog}$ is connected to the negative input of op-amp 50, while the positive input is grounded. Current source 44 is also connected through resistor 56 to the output node 59, which is turn is connected to the heart or other load, illustrated as $R_{load}$.

The output of op-amp 50 is connected to the inputs of transistors 52 and 53, each of which have the output terminal tied to output node 59. The drain of transistor 52 is connected to ground; the drain of transistor 53 is tied to ground in the constant voltage mode through op-amp 57 and resistor 58. Elements 57,58 act as a current sensor, providing a voltage across 58 which is indicative of the current through the load. Transistors 52, 53 are selected to operate in their linear regions, and are provided so that the current through 52 is a fixed multiple of that through 53, eg, the current through 52 is about 200 times that through 53, whatever the output current. This can be achieved, by ratio-ing of the two transistors, e.g., by using GMOS and connecting sources and drains to provide two GMOS transistors having relative current flows of about 200:1. It is to be noted that while the GMOS configuration is preferred, other transistor types of fixed-area ratios can be employed within the scope of the invention, the important feature being that they provide the desired current ratio when operated linearly. Concluding the account of elements in the circuit of FIG. 3A, a resistor 56 is switchably connected between the minus input of op-amp 50 and node 59 in the voltage mode; and the I input of op-amp 50 is switchably connected to the drain of transistor 53 in the current mode.

Figure 3B:
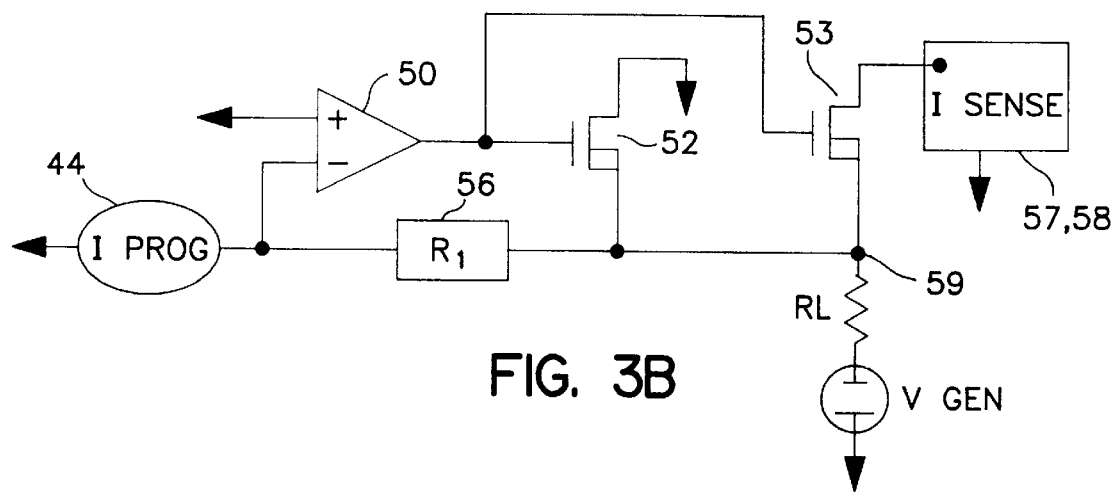
FIG. 3B is an equivalent circuit diagram of the output stage when in the constant voltage mode; and FIG.

Referring now to FIG. 3B, there is seen the configuration of the output stage when the switches are in position (1). Here, the current $I_{prog}$ is connected to flow directly across resistor 56; since the negative input of op-amp 50 is held at virtual ground, the output node 59 is held at a fixed voltage, whatever the current through the load. The sensor circuit measures current through transistor 53, which is a fixed percentage of load current, thereby providing an indication of the current during delivery of a pulse. A current measurement is indicative of the load impedance, and can aid in determining the appropriate $V_{gen}$ setting in the constant current mode, for optimum efficiency, as discussed below in connection with FIG. 4A.

Figure 3C:
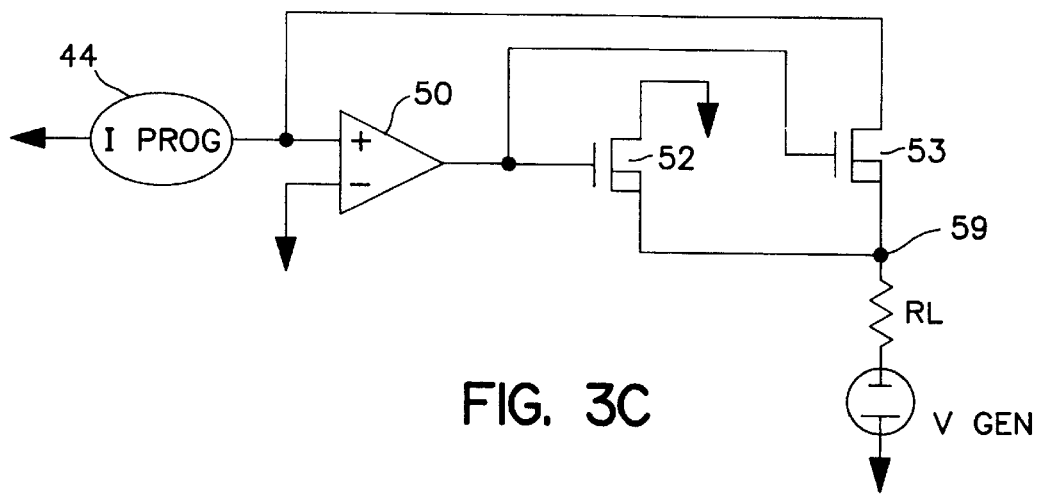

Referring to FIG. 3C, the effective circuit for constant current mode, it is seen that $I_{prog}$ is connected to the positive input of op-amp 50, and is also connected to be the current that flows through transistor 53. Since the current through transistor 52 is a fixed multiple of this current, the total current through R1 is fixed. In both cases, $I_{prog}$ can be determined precisely, enabling the desired control. Indeed, the circuit is simple enough that a gain-bandwidth of 50 MHz can be achieved. This enables excellent control for the duration of an output stimulus such as used in a cardiac pacemaker. Either mode can be provided with this simple but elegant architecture, which is not dependent upon close tolerances, matching resistors, etc. Indeed, the circuit only depends on the matching of the two transistors, which matching should be invariant with temperature and time. By lay-out and design techniques ordinary in the art, the matching can be substantially invariant over load current and load voltage.

The flow diagram of FIG. 4A illustrates how the output circuit of this invention can be used, such as in a cardiac pacemaker, for precise control of the mode, the amplitude, and for encoding data onto the pulse which is being generated and delivered. At 70, it is determined whether a stimulus pulse is to be delivered. In the pacemaker embodiment, this may occur when it has been determined whether a timer has timed out, or a natural signal has been sensed. After this, at 72, the device determines whether the delivered stimulus is to be constant voltage or constant current. If constant voltage, the circuit is switched at 73 to the configuration shown in FIG. 3B; and if-constant current mode is programmed, at 74 the circuit is switched to the configuration shown in FIG. 3C. Next, at 76, it is determined whether data is to be encoded onto the pulse form, by amplitude modulation. In the pacemaker embodiment, such data may represent pacemaker conditions, such as expected battery lifetime, or any other data adaptable to this form of simple transmission. If the pulse is to be modulated, the device goes to block 77 and obtains bits of data used to amplitude modulate one or more stimulus pulses. At 78, whether or not there is to be modulation, the device gets amplitude data, for setting $I_{prog}$, so as to control the pace amplitude of the output pulse. Then, at 80, $I_{prog}$ is controlled both with the amplitude and the modulation data, in a conventional manner, and the pulse is delivered as indicated at 90. If the pulse carries data to be transmitted to an external source, this data is sensed externally as indicated at 92, and decoded and outputted. The pulse waveform can be picked up externally by any conventional manner, such as by surface electrodes placed upon the patient.

Still referring to FIG. 4A, during delivery of a pulse, or pulse portion, the current (for a constant voltage pulse) or voltage (for a constant current pulse) is sensed, as illustrated at 95. Thus, for a constant voltage pulse, determination of the current through the load is used to set the value of $V_{GEN}$ for optimum efficiency in delivering a constant current pulse. Stated differently, a measure of load impedance is obtained, which is very important in optimally adjusting $V_{GEN}$. Similarly, during a constant current pulse or pulse portion, a measurement of $V_{OUT}$ at node 59 can be made, for efficient setting of $V_{GEN}$ for constant voltage operation. The adjustment of $V_{GEN}$ is made by a control such as illustrated at 42 in FIG. 1.

It is to be noted that other variations of this technique are within the scope of the invention. For example, this circuit provides the ability to provide a pulse having, for example, several portions with different amplitudes; or a first portion or component which is constant voltage, and a second which is constant current. As used in this specification, the term pulse is not limited in waveform, and in fact can embrace different shapes and also a series of pulses. If the device utilizing the output circuit of this invention is programmed to deliver a hybrid pulse having at least one constant voltage portion and at least one constant current portion, the sequence at 72, 73, 74 is modified to control switching between constant voltage and constant current during the interval embraced by the output pulse.

FIG. 4B shows a representation of a pulse produced in accordance with this system and method, illustrating 16 bits encoded on a constant voltage pulse having a time interval of about 200 microseconds. Although the bit transmission rate is relatively low, it is to be noted that this provides a supplemental wave transmitting a limited amount of data in a circumstance where the necessary programmer may not be available, as where the patient is in a remote location without access to the programmer.

There has thus been provided a simple but highly efficient output stage, for delivering pulses with finely controlled waveshapes, particularly in a medical device such as a pacemaker or other stimulator. The low power and excellent control properties make it useful for applications in implantable devices, and enable data transmission along with delivery of outputs used for therapeutic purposes. It is noted that engineering techniques within the state of the art, e.g., keeping voltages the same and lay-out matching, are important in achieving maximum circuit precision, and thus successful application of the circuit and techniques of this invention.

What is claimed is:

1. An output circuit for delivering a controllable output pulse to a patient, comprising:
    a pulse generating circuit for generating an output pulse;
    control mode means, for controlling said pulse generating circuit to operate in a constant voltage mode during the generation of a first portion of an output pulse and in a constant current mode during the generation of a second portion of the output pulse; and
    amplitude control means for controlling the amplitude of the output pulse as it is being delivered and means for delivering said output pulse to the tissue of a patient.

2. The output circuit as described in claim 1, wherein said amplitude control means comprises modulate means for modulating the amplitude level of the output pulse, thereby encoding data on said pulse.

3. The output circuit as described in claim 1, wherein said control mode means comprises programmable switch means adapted to be set at a programmed one of two settings corresponding to constant voltage or constant current output operation.

4. The output circuit as described in claim 3, wherein said amplitude control means comprises a low value constant current source.

5. The output circuit as described in claim 1, wherein said pulse generating circuit comprises two transistors connected to operate linearly, said two transistors carrying respective currents in a predetermined ratio when operating in their linear ranges.

6. The output circuit as described in claim 5, wherein said pulse generating circuit comprises an operational amplifier having an output connected to an input of each of said transistors, and said amplitude control means comprises a constant current source connected to an input of said operational amplifier.

7. The output circuit as described in claim 5, wherein said amplitude means comprises a constant current source, and said control mode means comprises a switching circuit for switchably connecting said constant current source to a first input of said operational amplifier for constant voltage operation, and to a second input of said operational amplifier for constant current operation.

8. The output circuit as described in claim 1, wherein said pulse generating circuit comprises a common output terminal for both said constant voltage and constant current modes.

9. A medical stimulator having an output circuit for generating stimulus pulses, said output circuit comprising mode means for controlling the delivery of each said stimulus pulses in a constant voltage mode during the generation of a first portion of an output pulse and in a constant current mode during the generation of a second portion of the output pulse, and amplitude control means for controlling the amplitude of each delivered stimulus pulse during the generation and delivery of the pulse and means for delivering the stimulus pulses to a heart of a patient.

10. The medical stimulator as described in claim 9, wherein said mode means comprises first data means for holding data representative of the desired mode of operation.

11. The medical stimulator as described in claim 9, wherein said amplitude control means comprises second data means for storing data representative of desired pulse amplitude.

12. The medical stimulator as described in claim 9, comprising current sense means for sensing current delivered with a stimulus pulse when said output circuit is in constant voltage mode.

13. The medical stimulator as described in claim 9, comprising modulate means for amplitude modulating a delivered stimulus pulse.

14. The medical stimulator as described in claim 13, wherein said stimulator further comprises means for delivering electrical stimulation to a heart of a patient.

15. The medical stimulator as described in claim 9, wherein said mode means comprises program means for programming delivery of a stimulus pulse with multiple portions having different amplitudes.

16. A controllable output circuit operable for delivering an output pulse to a patient in either a constant voltage or constant current mode, said circuit comprising:

a pulse generating circuit having two current-ratioed transistors, each resistor alternatively switchably connected to an input of an operational amplifier mode means for controlling said pulse generating circuit to operate in a selected one of said constant voltage mode during the generation of a first portion of an output pulse and in a constant current mode during the generation of a second portion of the output pulse, the mode means coupled to the pulse generator circuit;

amplitude means for controlling the constant voltage or constant current amplitude of a pulse delivered by said pulse generating circuit, the amplitude means coupled to the pulse generator circuit.

17. The output circuit as described in claim 16, wherein said mode means comprises a switch network.

18. The output circuit as described in claim 17, wherein said operational amplifier has two inputs; said amplitude means comprises a constant current source, and said switch circuit switchably connects said constant current source to said operational amplifier.

19. The output circuit as described in claim 18, wherein said pulse generating circuit comprises a resistance connected between said operational amplifier and one of said transistors.

20. The circuit as described in claim 16, comprising a voltage generator for powering said circuit, and means for varying the value of voltage output of said voltage generator.

21. The circuit as described in claim 16, further comprising a current sense circuit for sensing the current delivered by said pulse generator during constant voltage operation.

22. The circuit as described in claim 16, wherein said transistors are constructed of a fixed area ratio, and operate linearly to carry respective currents in accord with said ratio.

23. The circuit as described in claim 22, wherein said two transistors are a Gridmos pair.

24. Medical apparatus for cyclically generating stimulus pulses for delivery to a patient, comprising:

a pulse output circuit to generate an output pulse; and mode means operable each cycle for controlling said output circuit to operate in a constant voltage mode for a first portion of a generated output pulse and in a constant current mode for a second portion of the generated output pulse and means for delivering said generated output pulse to a heart of a patient.

25. The apparatus as described in claim 24, comprising amplitude control means operable each cycle for controlling the amplitude of a generated stimulus pulse while it is being delivered.

26. The apparatus as described in claim 24, comprising current sense means for sensing current when a constant voltage pulse is delivered.

27. The apparatus as described in claim 26, comprising voltage generator means for powering said pulse output circuit, and adjust means for adjusting the output of said output circuit as a function of said means for sensing.

\* \* \* \* \*